(12) United States Patent
Yip et al.

(10) Patent No.: US 11,154,431 B1
(45) Date of Patent: Oct. 26, 2021

(54) ABSORBENT GARMENT AND METHOD OF MANUFACTURE THEREOF

(71) Applicant: Mast Industries (Far East) Limited, Kowloon (HK)

(72) Inventors: Suet Hing Yip, Tai Wai (HK); Fung Yee Debby Au, Tai Po (HK)

(73) Assignee: Mast Industries (Far East) Limited, Kowloon (HK)

( * ) Notice: Subject to any disclaimer, the term of this patent is extended or adjusted under 35 U.S.C. 154(b) by 0 days.

(21) Appl. No.: 17/221,326

(22) Filed: Apr. 2, 2021

Related U.S. Application Data

(60) Provisional application No. 63/110,554, filed on Nov. 6, 2020.

(51) Int. Cl.
*A61F 13/49* (2006.01)
*A41B 9/00* (2006.01)
*A41B 17/00* (2006.01)
*A61F 13/15* (2006.01)

(52) U.S. Cl.
CPC ........ *A61F 13/49006* (2013.01); *A41B 9/001* (2013.01); *A41B 17/00* (2013.01); *A61F 13/15747* (2013.01)

(58) Field of Classification Search
CPC ......... A61F 13/49006; A61F 13/15747; A41B 9/001; A41B 17/00
See application file for complete search history.

(56) References Cited

U.S. PATENT DOCUMENTS

| | | |
|---|---|---|
| 3,489,149 A | 1/1970 | Larson |
| 3,608,551 A | 9/1971 | Saburo |
| 4,044,769 A | 8/1977 | Papajohn |
| 4,352,356 A | 10/1982 | Tong |
| 4,560,381 A | 12/1985 | Southwell |
| 4,573,987 A | 3/1986 | Lamb, Jr. |
| 4,718,902 A | 1/1988 | Bonito |
| 4,781,962 A | 11/1988 | Zamarripa |
| 4,813,950 A | 3/1989 | Branch |
| 5,151,092 A | 9/1992 | Buell et al. |
| 5,167,897 A | 12/1992 | Weber et al. |
| 5,217,782 A | 6/1993 | Moretz et al. |

(Continued)

FOREIGN PATENT DOCUMENTS

| | | |
|---|---|---|
| AU | 2010229644 B2 | 7/2013 |
| AU | 2015202737 A1 | 11/2015 |

(Continued)

*Primary Examiner* — Michele M Kidwell
(74) *Attorney, Agent, or Firm* — Andrus Intellectual Property Law, LLP

(57) ABSTRACT

A garment comprises a main body including a front portion, a back portion, and a gusset connecting the front portion and the back portion. The gusset has left and right lateral edges partially defining respective left and right leg openings of the garment. A layer of absorbent material is coupled to an inner face of the main body at least at the gusset. A layer of waterproof material is sandwiched between the main body and the layer of absorbent material. Left and right elastic bands couple the layer of absorbent material and the layer of waterproof material to the main body along the respective left and right lateral edges of the gusset. A method for manufacturing the absorbent garment is also provided.

17 Claims, 7 Drawing Sheets

(56) References Cited

U.S. PATENT DOCUMENTS

| | | |
|---|---|---|
| 5,291,617 A | 3/1994 | Moretz et al. |
| 5,308,346 A | 5/1994 | Sneller et al. |
| 5,342,338 A | 8/1994 | Roe |
| 5,360,420 A | 11/1994 | Cook et al. |
| 5,368,910 A | 11/1994 | Langdon |
| 5,392,467 A | 2/1995 | Moretz et al. |
| 5,449,352 A | 9/1995 | Nishino et al. |
| 5,500,270 A | 3/1996 | Langdon et al. |
| 5,507,895 A | 4/1996 | Suekane |
| 5,518,801 A | 5/1996 | Chappell et al. |
| 5,546,607 A | 8/1996 | Roberts |
| 5,562,648 A | 10/1996 | Peterson |
| 5,651,779 A | 7/1997 | Burrell |
| 5,665,452 A | 9/1997 | Langdon et al. |
| 5,669,902 A | 9/1997 | Sivilich |
| 5,693,169 A | 12/1997 | Langdon et al. |
| H1732 H | 6/1998 | Johnson |
| 5,778,457 A | 7/1998 | Conway |
| H1746 H | 8/1998 | Carrier et al. |
| 5,851,204 A | 12/1998 | Mizutani |
| 5,879,487 A | 3/1999 | Vella |
| 5,899,895 A | 5/1999 | Robles et al. |
| 6,041,446 A | 3/2000 | Braunstein et al. |
| 6,117,523 A | 9/2000 | Sugahara |
| 6,120,487 A | 9/2000 | Ashton |
| 6,174,303 B1 | 1/2001 | Suprise et al. |
| 6,231,554 B1 | 5/2001 | Menard |
| 6,240,569 B1 | 6/2001 | Van Gompel et al. |
| 6,355,330 B1 | 3/2002 | Koslow et al. |
| 6,381,994 B1 | 5/2002 | Lee |
| 6,610,901 B2 | 8/2003 | McMahon-Ayerst et al. |
| 6,848,121 B1 | 2/2005 | Halid |
| 6,861,520 B1 | 3/2005 | Todd et al. |
| 7,008,887 B2 | 3/2006 | Rearick et al. |
| 7,083,604 B2 | 8/2006 | Sakaguchi |
| 7,156,828 B2 | 1/2007 | Ostrow |
| 7,166,095 B1 | 1/2007 | Coates |
| RE39,919 E | 11/2007 | Dodge et al. |
| 7,322,966 B1 | 1/2008 | Deerin |
| 7,842,625 B1 | 11/2010 | Stockton et al. |
| 7,951,128 B1 | 5/2011 | Lewis |
| 8,117,675 B2 | 2/2012 | Strange et al. |
| 8,123,735 B2 | 2/2012 | Deerin |
| 8,318,615 B1 | 11/2012 | Filteau et al. |
| 8,460,265 B1 | 6/2013 | Calender |
| D701,018 S | 3/2014 | Wexler |
| D716,020 S | 10/2014 | Dunbar et al. |
| 8,935,813 B2 | 1/2015 | O'Leary |
| 8,968,266 B2 | 3/2015 | Kumar |
| 9,011,403 B2 | 4/2015 | De Bruin et al. |
| 9,980,861 B2 | 5/2018 | Deerin |
| 10,206,810 B2 | 2/2019 | Palmer |
| 10,231,885 B2 | 3/2019 | Hovey |
| D864,522 S | 10/2019 | Benavides |
| 10,441,479 B2 | 10/2019 | Griffiths |
| 10,441,480 B2 | 10/2019 | Griffiths |
| 10,512,563 B2 | 12/2019 | Rhodes |
| 10,555,841 B2 | 2/2020 | Png et al. |
| 10,750,793 B1 | 8/2020 | Theodoridis |
| 10,828,864 B2 | 11/2020 | Roup et al. |
| 10,864,123 B2 | 12/2020 | Yao et al. |
| 2001/0016721 A1 | 8/2001 | Salerno et al. |
| 2002/0013560 A1 | 1/2002 | Erspamer et al. |
| 2003/0004488 A1 | 1/2003 | Ashton et al. |
| 2003/0124927 A1 | 7/2003 | Waldroup et al. |
| 2003/0143376 A1 | 7/2003 | Toyoshima et al. |
| 2004/0230175 A1 | 11/2004 | Rainville-Lonn et al. |
| 2005/0055002 A1 | 3/2005 | Welicia |
| 2005/0090795 A1 | 4/2005 | Coleman |
| 2006/0070163 A1 | 4/2006 | Beck et al. |
| 2006/0105005 A1* | 5/2006 | Marenick ............... A61K 8/922 424/401 |
| 2008/0108962 A1 | 5/2008 | Furuta et al. |
| 2008/0114327 A1 | 5/2008 | Barge |
| 2008/0275415 A1 | 11/2008 | Wheeler et al. |
| 2009/0240224 A1 | 9/2009 | Underhill et al. |
| 2009/0247977 A1 | 10/2009 | Takeuchi et al. |
| 2010/0137773 A1 | 6/2010 | Gross et al. |
| 2010/0222759 A1 | 9/2010 | Hammons et al. |
| 2010/0249736 A1 | 9/2010 | Png et al. |
| 2011/0048077 A1 | 3/2011 | Warren et al. |
| 2012/0071849 A1 | 3/2012 | Kumar |
| 2012/0180198 A1 | 7/2012 | Ruggieri |
| 2012/0220976 A1 | 8/2012 | Morse et al. |
| 2013/0072888 A1 | 3/2013 | Zorin |
| 2014/0039432 A1 | 2/2014 | Dunbar et al. |
| 2014/0257228 A1 | 9/2014 | Chen-Yee et al. |
| 2014/0378935 A1 | 12/2014 | Shikokuchuo-Shi et al. |
| 2015/0011957 A1 | 1/2015 | Cloutier et al. |
| 2015/0290049 A1 | 10/2015 | Riha-Scott et al. |
| 2016/0184146 A1* | 6/2016 | Tulk ................... A61F 13/8405 514/560 |
| 2018/0014983 A1 | 1/2018 | Jayasuriya et al. |
| 2019/0209395 A1 | 7/2019 | Hovey |
| 2019/0380886 A1 | 12/2019 | Hammond |
| 2020/0170851 A1 | 6/2020 | Png et al. |
| 2020/0222256 A1 | 7/2020 | Chong |
| 2020/0246203 A1 | 8/2020 | Tulk et al. |
| 2020/0297556 A1 | 9/2020 | Png et al. |
| 2020/0337912 A1 | 10/2020 | Kwan |
| 2020/0375817 A9 | 12/2020 | Griffiths |
| 2020/0383393 A1 | 12/2020 | Caden |
| 2021/0177676 A1 | 6/2021 | Kajanthan et al. |

FOREIGN PATENT DOCUMENTS

| | | | |
|---|---|---|---|
| AU | 2017254823 A1 | 11/2017 | |
| AU | 2019204873 B2 | 11/2020 | |
| BE | 1010279 A5 | 5/1998 | |
| CA | 2126280 A1 | 12/1994 | |
| CA | 2126281 A1 | 12/1994 | |
| CA | 2152135 A1 | 12/1995 | |
| CA | 2238735 C | 2/2003 | |
| CA | 2780213 A1 | 12/2013 | |
| CA | 2827795 C | 12/2014 | |
| CA | 2718101 C | 6/2016 | |
| CA | 2961668 C | 7/2018 | |
| CA | 2945296 C | 2/2019 | |
| CA | 2942869 C | 10/2019 | |
| CN | 200983836 Y | 12/2007 | |
| CN | 201286800 Y | 8/2009 | |
| CN | 106456385 A | 2/2017 | |
| CN | 210765733 U | 6/2020 | |
| CN | 211227574 U | 8/2020 | |
| CN | 211394833 U | 9/2020 | |
| CN | 212036015 U | 12/2020 | |
| CN | 212375487 U | 1/2021 | |
| CN | 212505287 U | 2/2021 | |
| DE | 4429251 A1 | 2/1996 | |
| DE | 202004019377 U1 | 3/2005 | |
| EP | 0861647 A2 | 9/1998 | |
| EP | 1232857 A2 | 7/2003 | |
| EP | 2249671 B1 | 7/2014 | |
| EP | 2043580 B1 | 9/2014 | |
| EP | 2412353 A2 | 4/2015 | |
| EP | 2879534 B1 | 3/2017 | |
| EP | 3128970 A1 | 11/2017 | |
| EP | 3046592 B1 | 9/2018 | |
| EP | 3 437 604 A1 * | 2/2019 | ............ A61F 13/49 |
| EP | 2991605 B1 | 3/2020 | |
| EP | 3674074 A1 | 7/2020 | |
| FR | 3077981 A1 | 8/2019 | |
| GB | 2176692 B | 7/1989 | |
| GB | 2508089 B | 8/2015 | |
| GB | 2566464 A | 3/2019 | |
| JP | H10292204 A | 11/1998 | |
| JP | H11137590 A | 5/1999 | |
| JP | 2006002255 A | 1/2006 | |
| JP | 3967961 B2 | 8/2007 | |
| JP | 4073391 B2 | 4/2008 | |
| JP | 4090417 B2 | 5/2008 | |
| JP | 2017513671 A | 6/2017 | |
| KR | 694187 B1 | 3/2007 | |
| KR | 10-1940297 B1 | 1/2019 | |

(56) References Cited

FOREIGN PATENT DOCUMENTS

| | | |
|---|---|---|
| KR | 10-2026925 B1 | 9/2019 |
| KR | 10-2082283 B1 | 2/2020 |
| KR | 10-2267118 B1 | 6/2021 |
| NZ | 626874 A | 8/2014 |
| WO | WO 1986005386 A1 | 9/1986 |
| WO | WO 1993012746 A1 | 7/1993 |
| WO | WO 2008093435 A1 | 8/2008 |
| WO | WO 2010024120 A1 | 3/2010 |
| WO | WO 2013146928 A1 | 10/2013 |
| WO | WO 2014050595 A1 | 4/2014 |
| WO | WO 2014054649 A1 | 4/2014 |
| WO | WO 2014194574 A1 | 12/2014 |
| WO | WO 2014200121 A1 | 12/2014 |
| WO | WO 2015177307 A1 | 11/2015 |
| WO | Wo 2019036783 A1 | 2/2019 |
| WO | WO 2019162615 A1 | 8/2019 |
| WO | WO 2019221317 A1 | 11/2019 |
| WO | WO 2020056949 A1 | 3/2020 |
| WO | WO 2020065299 A1 | 4/2020 |
| WO | WO 2020084600 A1 | 4/2020 |
| WO | WO 2020121176 A1 | 6/2020 |

\* cited by examiner

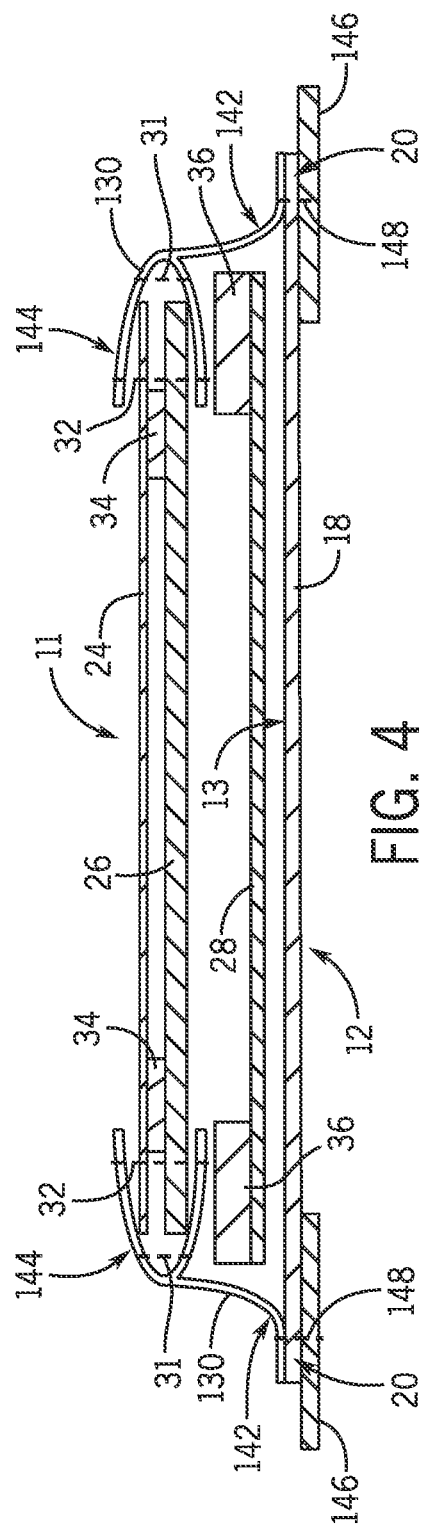
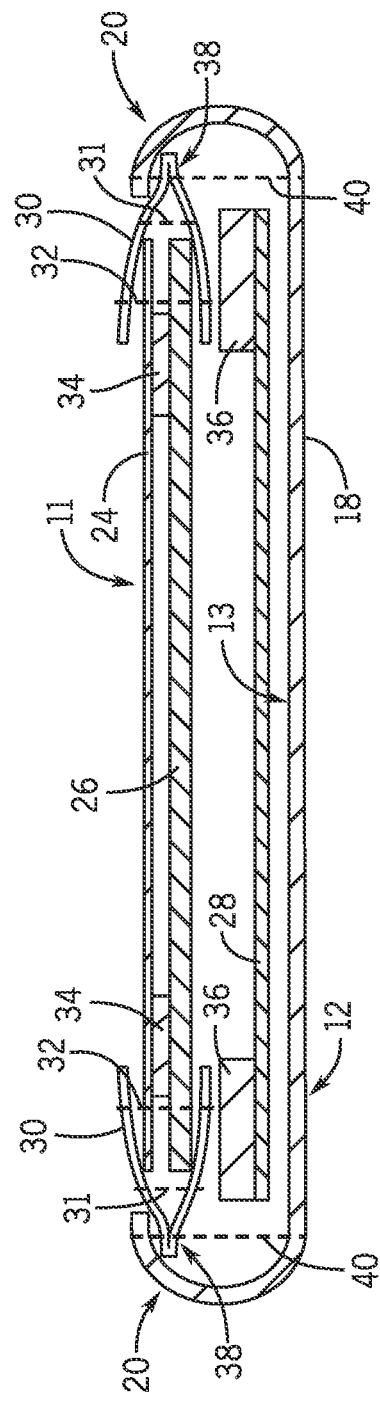
FIG. 4
FIG. 5

ABSORBENT GARMENT AND METHOD OF MANUFACTURE THEREOF

CROSS-REFERENCE TO RELATED APPLICATION

The present application claims the benefit of U.S. Provisional Application Ser. No. 63/110,554, filed Nov. 6, 2020, which is hereby incorporated by reference herein in its entirety.

FIELD

The present application relates to garments, and more specifically to garments with an absorbent gusset that is configured to be worn adjacent a wearer's crotch.

BACKGROUND

U.S. Patent Application Publication No. 2014/0039432 discloses an undergarment including a multilayer leak-proof pad to wick moisture, impede bacteria, prevent leaks, and resist stain.

U.S. Patent Application Publication No. 2018/0014983 discloses a liquid absorbing pad for use in clothing, comprising: a liquid permeable layer; a functional layer over the liquid impermeable layer; and a liquid impermeable barrier material, wherein the functional layer is capable of acquiring and distributing liquid and/or absorbing liquid and the liquid impermeable barrier material is bonded to at least the liquid impermeable layer and the functional layer around the periphery of said layers by a bonding means, provided that the bonding means is not stitching. The liquid absorbable pad may form part of a garment.

U.S. Patent Application Publication No. 2020/0222256 discloses a protective insert operatively attachable to an inner, body-facing layer of a garment. The protective insert generally comprises, a first, operatively inner layer comprising a moisture-wicking, odor resistance, fluid absorbent fiber with or without a waterproof laminate-film; and a second, operatively outer layer comprising a breathable, odor resistant, water repellent fiber to further prevent fluid passage through the garment; wherein the operatively inner layer faces the body of a user while the operatively outer layer faces away from the body of a user, in use U.S. Patent Application Publication No. 2020/0246203 discloses an undergarment article having a fabric layer for wearing about a pelvic region of a person, a water-repellent layer coupled to a crotch portion of the fabric layer to form an inner chamber, and an inner pad disposed within the inner chamber between the water-repellent layer and the fabric layer. The inner pad is resistant to heat and includes a liquid-absorbent layer and a waterproof layer. The liquid-absorbent layer contacts the water-repellent layer and is effective for absorbing a volume of liquid greater than 2 fluid ounces. The waterproof layer is effective for restricting liquid from reaching the fabric layer. The crotch portion of the fabric layer and the water-repellent layer can be substantially elastic in at least one of a lateral direction and a longitudinal direction of the crotch portion. Methods for using the undergarment, kits and uses of the undergarment are also disclosed.

U.S. Pat. No. 7,322,966 discloses a washable, reusable garment for retention of body fluids when worn on a person's lower body part. The garment has a crotch portion and a body portion. The crotch portion has an absorbent composite, and a pocket adapted for receiving a removable absorbent pad. The body portion has a waist opening and is seamless except where attached to the crotch portion. The body portion and the crotch portion together form first and second leg openings.

U.S. Pat. No. 8,117,675 discloses a waterproof panty that has rolled over welded seams. The rolled over welded seam will inhibit the leaking of bodily fluids at the leg openings caused by stitching and wicking. The panty has an outer shell and an inner panty layer. The outer shell a continuous cut formed of a soft blend laminated fabric. It is liquid proof, breathable, hypo-allergenic, stain resistant, and elastic. It is cut to form a waist opening and two leg openings. If desired stretchable lace or elastic side portions can be provided. The inner panty lining is a breathable soft blend fabric and includes a front portion, back portion and a crotch portion. The crotch portion is double layered for added dryness. The inner panty layer is cut to the full design of the panty having a waist opening and two leg openings. This overall design provides the user peace of mind and security with a stylish, lightweight, comfortable, waterproof panty.

U.S. Pat. No. 8,460,265 discloses a washable female undergarment designed for comfort and for alleviating leakage. The undergarment comprises an outer layer of a stretchable fabric, an inner layer of an absorbent fabric, and a main absorbent layer positioned between the inner and outer layers in the crotch area. The three layers are permanently secured together to form a reusable reliant undergarment.

U.S. Pat. No. 10,231,885 discloses an undergarment configured to help absorb leaks of bodily fluids from a person suffering from mild to moderate incontinence or other conditions including a main body made of a material that allows the absorption of bodily fluids and a crotch piece made of a material that allows the absorption of bodily fluids that overlays the crotch portion of the main body. The crotch piece of the undergarment can extend high enough and be wide enough on the front side of the garment's main body so as to offer an adequate area of protection to the user.

U.S. Pat. No. 10,441,479 discloses an undergarment including a body portion having an upper edge defining a waistband, two leg openings and a crotch region between the leg openings; an absorbent pad on the inside of the body portion within at least the crotch region, the absorbent pad having an inner region and a peripheral region, wherein the thickness of the absorbent pad in the peripheral region is less than the thickness of the absorbent pad in the inner region; and elastic bonding film lining each of the two leg openings while overlying respective portions of the peripheral region of the absorbent pad thereby to bond the absorbent pad and the body portion. A method of manufacturing an undergarment is provided.

U.S. Pat. No. 10,555,841 discloses protective garments comprising an inner surface or portion of an inner surface with both absorbent and stain resistant properties while maintaining the soft feel, breathability and aesthetic properties associated with traditional "non protective" intimate apparel. The fabrics and methods of constructing the garments are also disclosed herein.

International Patent Application Publication No. 2019/162615 discloses leaktight underpants comprising a fabric body with a waist opening and a pair of leg openings. They comprise a front part and a rear part, the front and rear parts being fastened together by lateral seams. The leaktight underpants comprise, in the crotch part, a protective assembly, the protective assembly comprising an absorbent layer and a draining layer, which are fastened to the edge portion of each leg opening. The absorbent layer or the draining layer is fastened to the lateral seams of the front or rear parts of the fabric body, only the absorbent layer, or only the draining layer, being fastened to the rear edge or to the front edge, respectively, delimiting the waist opening.

International Patent Application Publication No. 2020/121176 discloses a multi-layer liquid absorbing and retaining textile assembly. The textile assembly comprises at least a first layer, a second layer and an intermediate layer. The intermediate layer is constructed as a warp knitted spacer fabric having a plurality of sections with at least one section being proximal to the first layer and at least another section being proximal to the second layer. The first layer is adapted to transfer liquid from a first side of the textile assembly to the intermediate layer. The intermediate layer is adapted to receive and transfer liquid to the second layer. The second layer is adapted to retain the liquid at or proximal to a second side of the textile assembly that is oppositely facing to the first side.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

According to one example of the present disclosure, a garment comprises a main body including a front portion, a back portion, and a gusset connecting the front portion and the back portion. The gusset has left and right lateral edges partially defining respective left and right leg openings of the garment. A layer of absorbent material is coupled to an inner face of the main body at least at the gusset. A layer of waterproof material is sandwiched between the main body and the layer of absorbent material. Left and right elastic bands couple the layer of absorbent material and the layer of waterproof material to the main body along the respective left and right lateral edges of the gusset.

According to another example, a method for manufacturing an absorbent garment comprises providing a main body including a front portion, a back portion, and a gusset connecting the front portion and the back portion, wherein the gusset has left and right lateral edges configured to partially define respective left and right leg openings of the garment. A layer of absorbent material is provided, which is sized and shaped to fit on the gusset and has left and right lateral edges configured to extend alongside the respective left and right lateral edges of the gusset. The method includes attaching left and right elastic bands along the respective left and right lateral edges of the layer of absorbent material. A layer of waterproof material is provided, which is sized and shaped to fit on the gusset and has left and right lateral edges configured to extend alongside the respective left and right lateral edges of the gusset. The left and right lateral edges of the layer of waterproof material are attached to the respective left and right elastic bands. The method includes attaching the left and right elastic bands to the respective left and right lateral edges of the gusset to couple the layer of absorbent material and the layer of waterproof material to the main body.

BRIEF DESCRIPTION OF DRAWINGS

Examples of garments and portions thereof are described with reference to the following Figures. The same numbers are used throughout the Figures to reference like features and like components.

FIG. 4 is a schematic cross-sectional view of an alternative configuration for the gusset.

FIG. 5 is a schematic cross-sectional view of another alternative configuration for the gusset.

DETAILED DESCRIPTION

The present application relates to garments, and more specifically to garments having an absorbent gusset area configured to cover a wearer's crotch, although the absorbent portions of the garment could extend beyond the gusset area as well. For example, the present application relates to panties or swimwear capable of absorbing bodily fluids such as urine, menstrual fluid, vaginal discharges, and/or sweat. The panties or swimwear can be any style and can have any trim, which details are not limiting on the scope of the present disclosure. In other examples, the garment is a pair of tights, a pair of pantyhose, a bodysuit, or any other type of garment that is configured to be worn directly against a wearer's skin.

Figure 1:
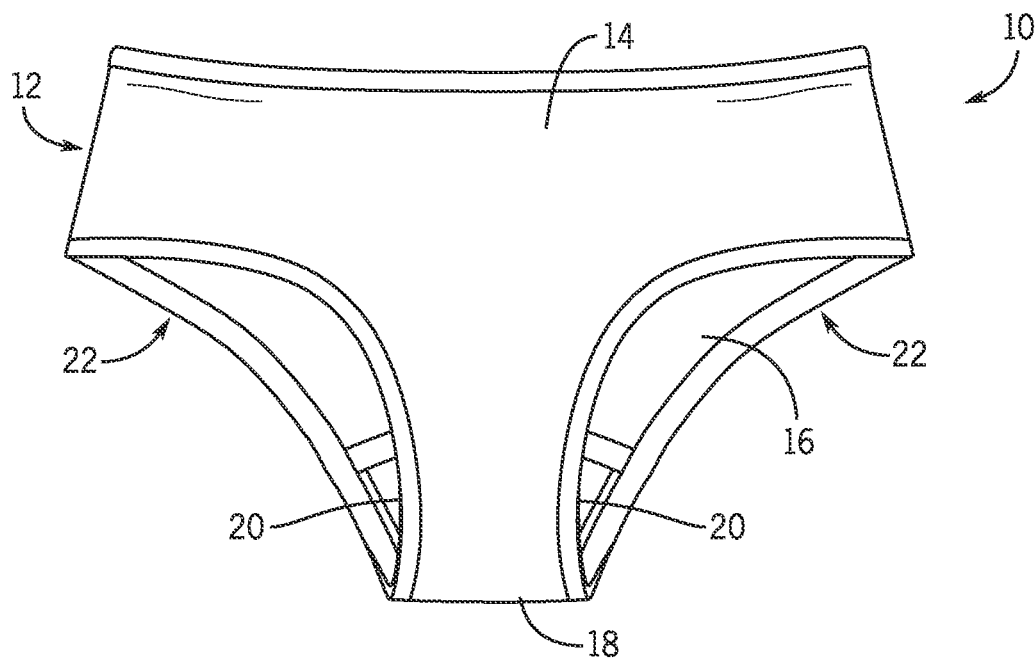
FIG. 1 is a front view of a garment according to the present disclosure.
Figure 2:
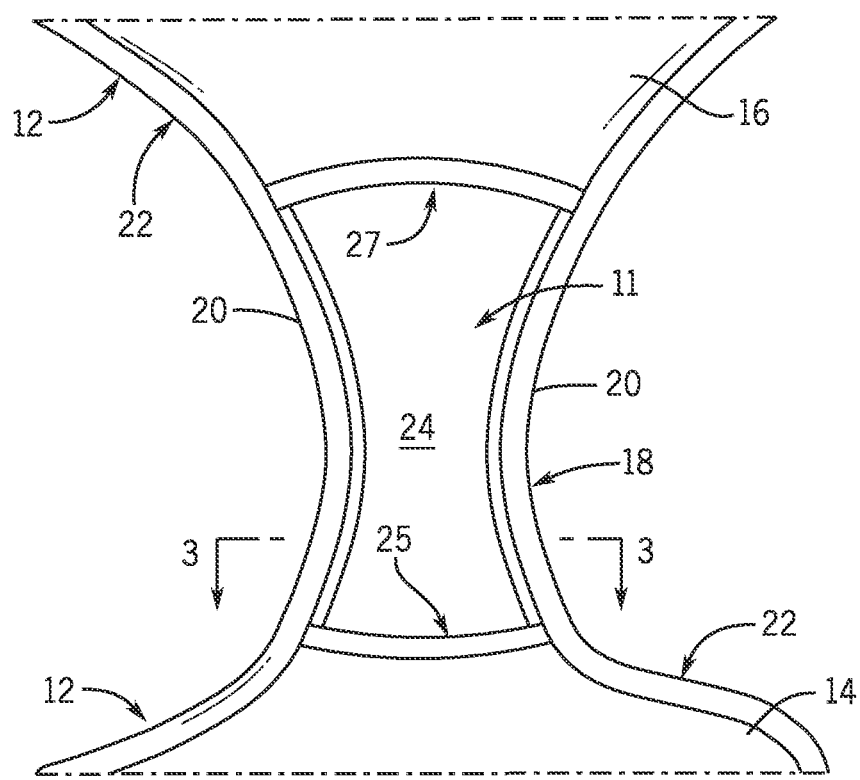
FIG. 2 is an interior view of the gusset of the garment.

FIG. 1 shows a front view of one example of the garment 10. Here, the garment 10 is a pair of panties, although note the garment 10 could instead be a pair of swim bottoms. The garment 10 has a main body 12 including a front portion 14, a back portion 16, and a gusset 18 connecting the front portion 14 and the back portion 16. The gusset 18 has opposite left and right lateral edges 20 partially defining respective left and right leg openings 22 of the garment 10. FIG. 2 shows the interior of the garment 10 with the hip portions of the garment 10 disconnected to show the extent of the gusset 18. A layer of liner material 24 can be seen covering a majority of the gusset 18. The layer of liner material 24 shows the extent of an absorbent assembly 11 of the garment 10 and covers a layer of absorbent material and a layer of waterproof material, which are also coupled to the gusset 18 as will be described further herein below. While the absorbent assembly 11 is coupled to the garment 10 at least at the gusset 18, it could extend into the front portion 14 or back portion 16, as noted hereinabove. Options for the absorbent assembly 11 of the garment 10 are described below.

Figure 3:
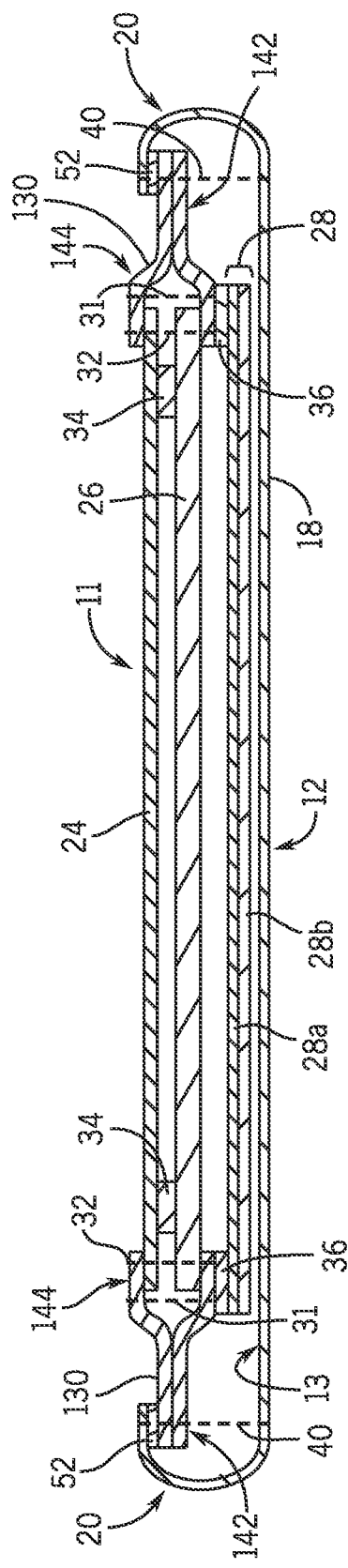
FIG. 3 is a schematic cross-sectional view taken along the line 3-3 shown in FIG. 2.

In one example, as shown in FIG. 3, a layer of absorbent material 26 is coupled to an inner face 13 of the main body 12 of the garment 10 at least at the gusset 18. A layer of waterproof material 28 is sandwiched between the main body 12 and the layer of absorbent material 26. The layer of liner material 24 is coupled to the layer of absorbent material 26 opposite the layer of waterproof material 28, such that the layer of absorbent material 26 is sandwiched between the layer of liner material 24 and the layer of waterproof material 28. In use, the layer of liner material 24 is configured to touch the wearer's skin while the garment 10 is worn. However, as will be described herein below, the layer of liner material 24 is optional. Left and right elastic bands 130 couple the optional layer of liner material 24, the layer of absorbent material 26, and the layer of waterproof material 28 to the main body 12 along the respective left and right lateral edges 20 of the gusset 18.

In one example, the left and right elastic bands 130 are folded around respective left and right lateral edges of each of the layer of liner material 24 and the layer of absorbent material 26 and then attached to the layers of liner material 24 and absorbent material 26 along the opposite lateral edges thereof. For example, the left and right elastic bands 130 are stitched to the layer of liner material 24 and the layer of absorbent material 26 where the left and right elastic bands 130 overlap the respective left and right lateral edges of each of the layer of liner material 24 and the layer of absorbent material 26, such as at stitch lines 32. Before this is done, the layer of liner material 24 can optionally be bonded to the layer of absorbent material 26 by way of heat-activated adhesive tape 34, such that the layer of liner material 24 is also bonded to the layer of absorbent material 26 laterally inwardly of where the left and right elastic bands 130 overlap and are stitched to the respective left and right lateral edges of each of the layer of liner material 24 and the layer of absorbent material 26. After the layers of liner material 24 and absorbent material 26 are stitched to the elastic bands 130, the layer of waterproof material 28 is attached to the elastic bands 130. More specifically, the layer of waterproof material 28 can be bonded to each of the left and right elastic bands 130 over stitches (at stitch lines 32) by which the left and right elastic bands 130 are stitched to the respective left and right lateral edges of each of the layer of absorbent material 26 and the layer of liner material 24, again such as by way of heat-activated adhesive tape 36.

The elastic bands 130 are folded around the opposite lateral edges of each of the layer of liner material 24 and the layer of absorbent material 26 in such a way that a laterally outer portion 142 of each folded elastic band 130 does not enclose the layer of liner material 24 or the layer of absorbent material 26 therein. The elastic bands 130 are stitched to the main body 12 along the opposite lateral edges 20 of the gusset 18 in a manner such that the stitching does not extend through the layer of liner material 24 and the layer of absorbent material 26, such as by stitching at these laterally outer portions 142 of the folded elastic bands 130 (see stitch lines 40). Although stitch lines 40 are shown as a single stitch, this may be a two-needle cover stitch, a zig-zag stitch, or any other known appropriate stitch.

In the example shown in FIG. 3, the folded elastic bands 130 are "Y-folded" elastic bands. The laterally inner portions 144 of the Y-folded elastic bands 130 form "V"-shaped folds, which enclose the respective outer lateral edges of the layer of liner material 24 and the layer of absorbent material 26. The outer lateral edges 20 of the gusset 18 fabric are folded around the "tail" of each "Y" at the laterally outer portions 142, and the outer lateral edges 20 of the gusset 18 fabric are then sewn to the laterally outer portions 142 of the elastic bands 130 through the tail of the elastic bands 130 and the fabric of the gusset 18, as shown by the stitch lines 40. In another example, the elastic bands 130 are sewn only to the upper folded-over portion of the fabric of the gusset 18. Because the main body 12 is folded over the left and right elastic bands 130 and attached to the left and right elastic bands 130 at the respective left and right lateral edges 20 of the gusset 18, this provides a clean, finished look to the leg openings 22 and presents comfortable, finished edges of the leg openings 22 that reduce the likelihood of chafing against a wearer's skin.

FIG. 4 illustrates a second example of a cross-section of an absorbent portion of an garment. The absorbent portion of the garment includes the same front portion 14, back portion 16, gusset 18 and other layers and connections noted herein above, which are labeled with like reference numbers and will not be described further herein. The elastic bands 130 are "Y-fold" elastic bands that each have the laterally inner portion 144 and the laterally outer portion 142. The laterally inner portions 144 are in the shape of a "V" and open inwardly such that the laterally outer edges of the layer of liner material 24 and the layer of absorbent material 26 can be inserted therein. As in the example of FIG. 3, the laterally outer portions 142 are the portions then stitched to the outer lateral edges 20 of the gusset 18 fabric, such as shown at stitch lines 148. Optional trim 146 (such as lace) can be sewn to the outer lateral edges 20 of the gusset 18 and to the laterally outer portions 142 of the elastic bands 130 at the same time. The layer of waterproof material 28 is shown as being bonded to the bottom of the laterally inner portions 144 of the elastic bands 130, but could alternatively or additionally be bonded to the laterally outer portions 142. In another example, the trim 146 and/or outer lateral edges 20 of the gusset 18 are folded over the laterally outer portions 142 of the elastic bands 130 and sewn thereto, along stitch lines 148.

FIG. 5 illustrates a third example of a cross-section of an absorbent portion of an garment. The absorbent portion of the garment includes the same front portion 14, back portion 16, gusset 18 and other layers and connections noted herein above, which are labeled with like reference numbers and will not be described further herein. However, in contrast to the examples in FIGS. 3 and 4, the folded elastic bands 30 are folded in the shape of a "V." The outer lateral edges 20 of the gusset 18 fabric are folded around the base of each "V", and the outer edges 20 of the gusset 18 fabric are then sewn to the laterally outer portions 38 of the elastic bands 30 through both folded-over layers of the elastic bands 30 and the fabric of the gusset 18, as shown by the stitch lines 40. In another example, the elastic bands 30 are sewn only to the upper folded-over portion of the fabric of the gusset 18. In some examples, each laterally outer portion 38 of each elastic band 30 can be sewn, adhered, or otherwise attached to itself laterally outwardly of where it overlaps the layer of liner material 24 and the layer of absorbent material 26, to form a sort of "faux" Y-fold elastic.

Because the left and right elastic bands 30, 130 are stitched to the main body 12 along the respective left and right lateral edges 20 of the gusset 18 laterally outwardly of where the left and right elastic bands 30, 130 overlap the respective left and right lateral edges of the layer of absorbent material 26 and the optional layer of liner material 24, the stitching at stitch lines 40, 148 does not extend through the liquid-absorbing portion(s) of the absorbent assembly 11, lessening the likelihood of leaks. Further lessening the likelihood of leaks, each of the left and right elastic bands 30, 130 can be stitched to itself laterally outwardly of and adjacent to where the left and right elastic bands 30, 130 overlap and are stitched to the respective left and right lateral edges of the layer of absorbent material 26 and the optional layer of liner material 24, as shown at stitch lines 31 in FIGS. 3-5. Such stitching at stitch lines 31 effectively creates a "cuff" around the absorbent portion(s) of the absorbent assembly 11, and if the elastic bands 30, 130 are treated with chemicals that make them waterproof or water resistant, as described herein below, this "cuff" can further prevent leaks from the absorbent portion(s) of the absorbent assembly 11. Furthermore, because the layer of waterproof material 28 is bonded to each of the left and right elastic bands 30, 130 over stitches (at stitch lines 32) by which the left and right elastic bands 30, 130 are stitched to each of the respective left and right lateral edges of the layer of absorbent material 26 and the layer of liner material 24, any liquid that might otherwise tend to leak from the absorbent portion(s) of the absorbent assembly 11 due to such stitch lines 32 is maintained on the inner face of the layer of waterproof material 28 (i.e., not on the face that contacts the main body 12 fabric).

Figure 9:
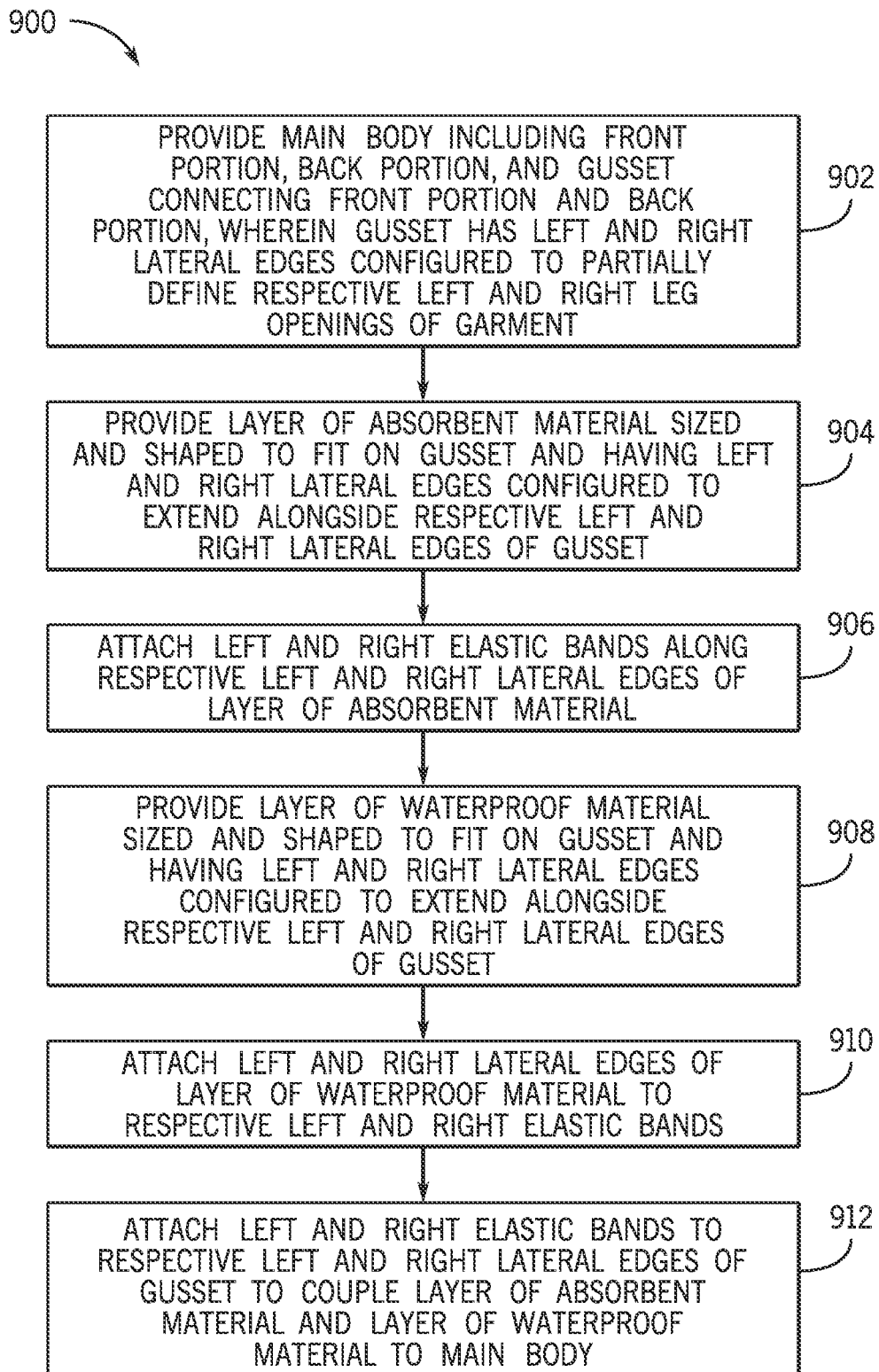
FIG. 9 shows one example of a method for manufacturing a garment according to the present disclosure.

As shown in FIG. 9, a method 900 for manufacturing an absorbent garment 10 is also disclosed. The method comprises providing a main body 12 including a front portion 14, a back portion 16, and a gusset 18 connecting the front portion 14 and the back portion 16, wherein the gusset 18 has opposite left and right lateral edges 20 configured to partially define respective left and right leg openings 22 of the garment 10, as shown at 902. As shown at 904, the method includes providing a layer of absorbent material 26 sized and shaped to fit on the gusset 18 and having left and right lateral edges configured to extend alongside the respective left and right lateral edges 20 of the gusset 18. Note that the layer of absorbent material 26 can have the exact same (or similar) shape as the gusset 18, but is slightly smaller in the lateral direction than the gusset 18, such that the layer of absorbent material 26 can fit on the gusset 18 without hanging over the lateral edges 20 thereof.

Figure 11:
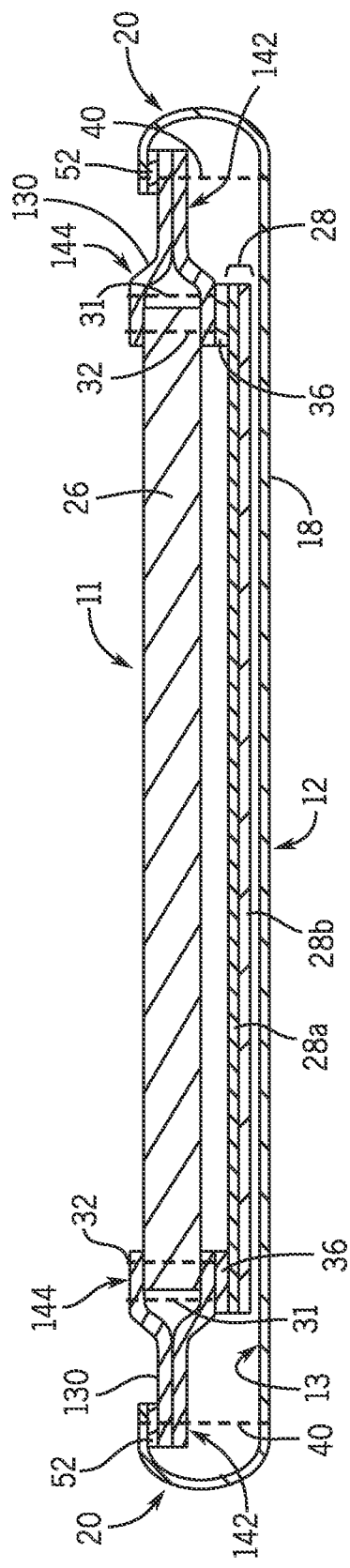
FIG. 11 is a schematic cross-sectional view of an alternative configuration for the gusset.

The method includes attaching left and right elastic bands 30, 130 along the respective left and right lateral edges of the layer of absorbent material 26, as shown at 906. For example, as shown and described with respect to FIGS. 3-5, the method includes folding the left and right elastic bands 30, 130 around the respective left and right lateral edges of the layer of absorbent material 26. Note that in this example of the method, no layer of liner material 24 is provided. This may be desirable if the finished garment 10 is to be lightweight and thin in the gusset 18. For example, as shown in FIG. 11, the layer of absorbent material 26 could be the layer that touches the wearer's skin (and thus acts as a dual "liner"/absorbent layer). As will be described further herein below, this layer of liner/absorbent material 26 can be a push-pull fabric.

Figure 6:
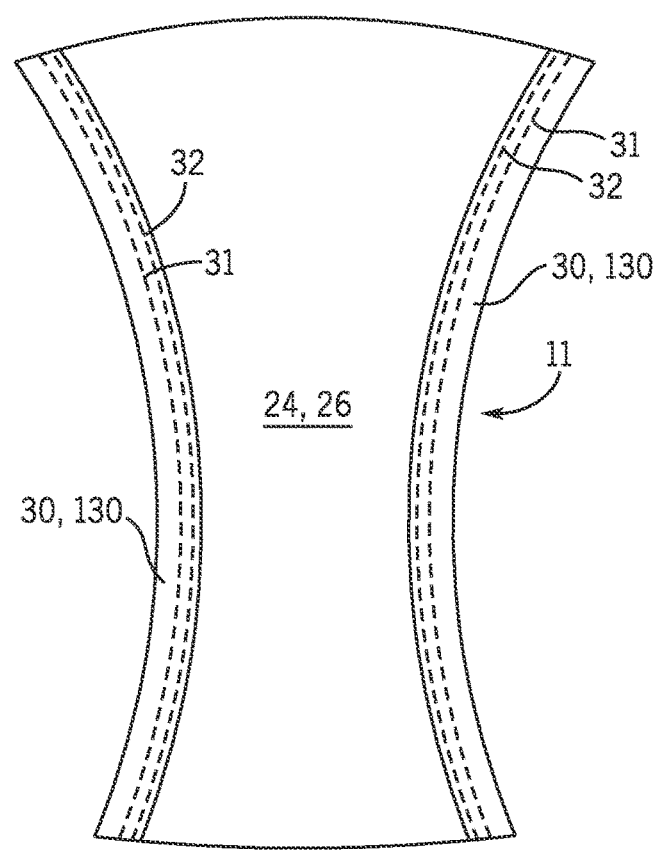
FIG. 6 illustrates a view of an inner face of an absorbent assembly configured to be attached to the gusset of the garment.

FIG. 6 shows the absorbent assembly 11 from an inner face (i.e., the face that is intended to touch the wearer's skin once the absorbent assembly 11 is attached to the gusset 18 of the main body 12) as it would appear at this point in the method of construction (i.e., after step 906). It can be seen that the elastic bands 30, 130 are sewn to themselves along stitch lines 31 at folded over portions, and are sewn at stitch lines 32 to the layer of absorbent material 26. In this particular example, the attaching of the left and right elastic bands 30, 130 along the respective left and right lateral edges of the layer of absorbent material 26 is done by stitching, but it could instead be done by bonding, such as with adhesive and/or ultrasonic waves.

Figure 7:
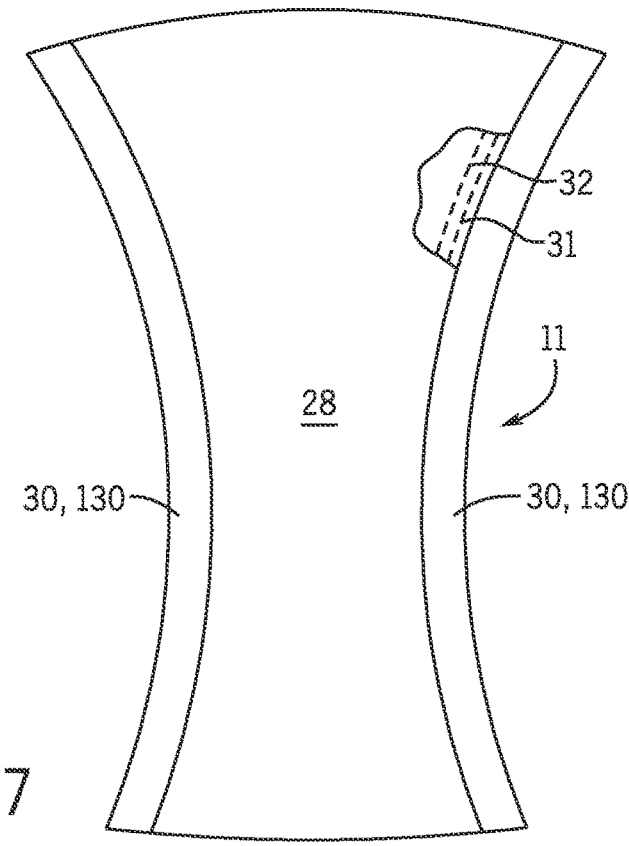
FIG. 7 illustrates a view of an outer face of the absorbent assembly of FIG. 6.

Returning to FIG. 9, as shown at 908, the method includes providing a layer of waterproof material 28 sized and shaped to fit on the gusset 18 and having left and right lateral edges configured to extend alongside the respective left and right lateral edges 20 of the gusset 18. Note that the layer of waterproof material 28 can have the exact same (or similar) shape as the gusset 18, but is slightly smaller in the lateral direction than the gusset 18 and larger in the lateral direction than the layer of absorbent material 26. This way, the layer of waterproof material 28 can fit on the gusset 18 without hanging over the lateral edges 20 thereof, but can also extend over the stitch lines 32 connecting the elastic bands 30, 130 to the layer of absorbent material 26. To that end, the method also includes attaching the left and right lateral edges of the layer of waterproof material 28 to the respective left and right elastic bands 30, 130, as shown at 910. Referring briefly to FIG. 7, which shows a view of the outer face of the absorbent assembly 11 before it is assembled onto the gusset 18, the method may include bonding (using for example adhesive tape 36, FIG. 3) the left and right lateral edges of the layer of waterproof material 28 to the respective left and right elastic bands 30, 130 over stitches (shown in part at 32) by which the left and right elastic bands 30, 130 are stitched to the respective left and right lateral edges of the layer of absorbent material 26. As noted above, this waterproofs the seam at stitch lines 32. The layer of waterproof material 28 may also be bonded to the respective left and right elastic bands 30, 130 over the stitch lines 31 where the elastic bands 30, 130 are stitched to themselves, thus further waterproofing the "cuff" formed by the folded-over elastic bands 30, 130. Thus, while the left and right elastic bands 30, 130 may be stitched to the layer of absorbent material 26, they are bonded to the layer of waterproof material 28 to improve waterproof performance.

Figure 8:
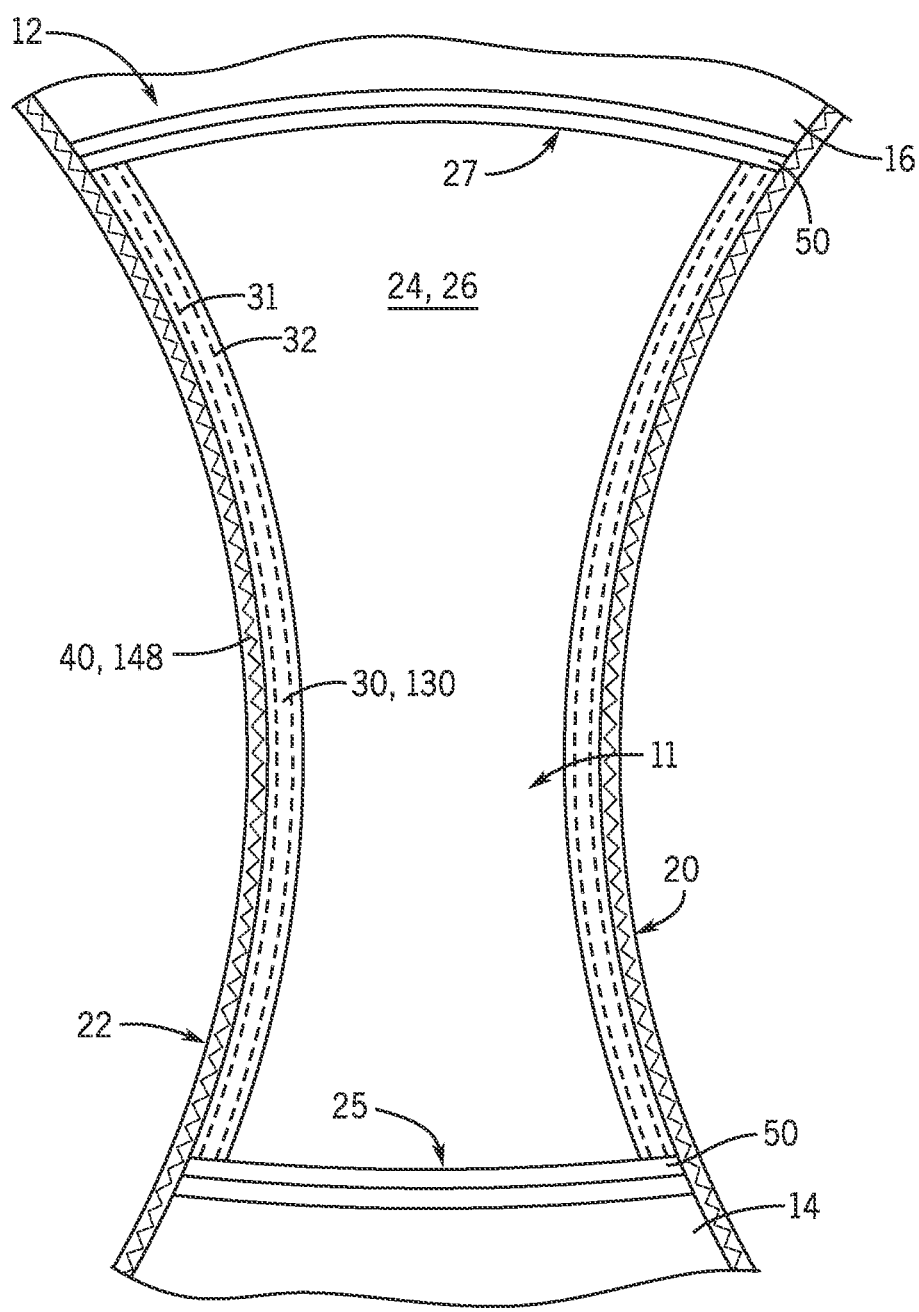
FIG. 8 illustrates a view of an inner face of the gusset of the garment, with the absorbent assembly of FIG. 6 attached thereto.

Returning to FIG. 9, as shown at 912, the method includes attaching the left and right elastic bands 30, 130 to the respective left and right lateral edges 20 of the gusset 18 to couple the layer of absorbent material 26 and the layer of waterproof material 28 to the main body 12. As shown in FIG. 8, which shows a view of the inner face of the absorbent assembly 11 after it has been coupled to the gusset 18, this may include attaching the left and right elastic bands 30, 130 to the main body 12 along the respective left and right lateral edges 20 of the gusset 18 laterally outwardly of where the left and right elastic bands 30, 130 overlap the respective left and right lateral edges of the layer of absorbent material 26. Compare stitch lines 40, 148 where the elastic bands 30, 130 are attached to the main body 12, to stitch lines 32, where the layer of absorbent material 26 is attached to the elastic bands 30, 130. As noted hereinabove with respect to FIG. 3, this step may include folding the fabric of the main body 12 over the left and right elastic bands 30, 130 and attaching the main body 12 to the left and right elastic bands 30, 130 at the respective left and right lateral edges 20 of the gusset 18. Thin, flat elastic bands 52 (FIG. 3) may be sewn to the main body 12 at the respective left and right lateral edges 20 of the gusset 18 and along the remainder of the leg openings 22 before the main body 12 is folded over and attached to the absorbent assembly 11 and to itself. (Note that these elastic bands 52 could be used in the same places in the construction of FIG. 5 as well, although not shown therein.)

Figure 10:
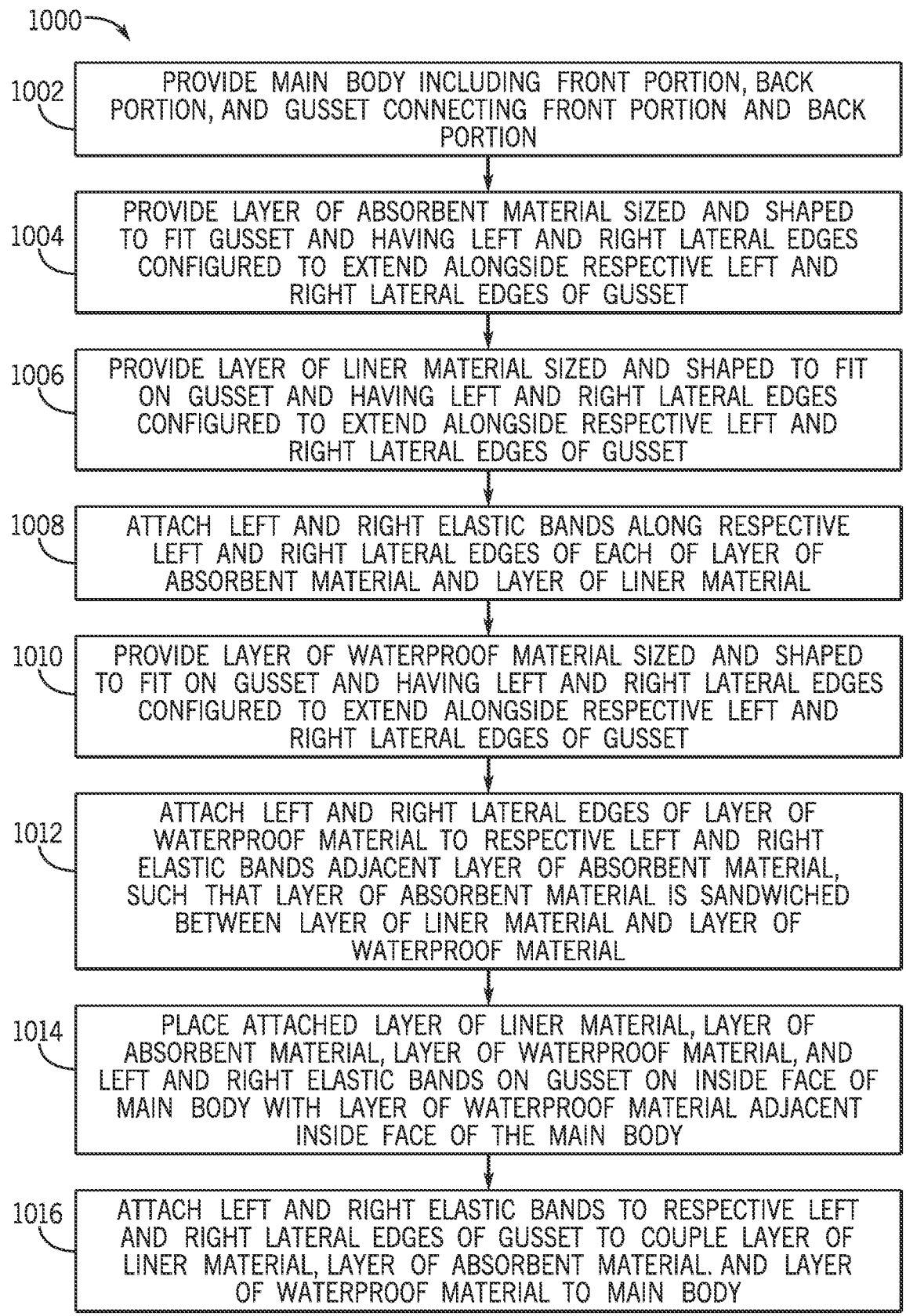
FIG. 10 shows another example of a method for manufacturing a garment according to the present disclosure.

FIG. 10 illustrates another method 1000 for manufacturing an absorbent garment 10 according to the present disclosure. The method 1000 comprises providing a main body 12 including a front portion 14, a back portion 16, and a gusset 18 connecting the front portion 14 and the back portion 16, wherein the gusset 18 has opposite left and right lateral edges 20 configured to partially define respective left and right leg openings 22 of the garment 10, as shown at 1002. As shown at 1004, the method includes providing a layer of absorbent material 26 sized and shaped to fit on the gusset 18 and having left and right lateral edges configured to extend alongside the respective left and right lateral edges 20 of the gusset 18. As shown at 1006, the method includes providing a layer of liner material 24 sized and shaped to fit on the gusset 18 and having left and right lateral edges configured to extend alongside the respective left and right lateral edges 20 of the gusset 18. Note that the layer of absorbent material 26 and the layer of liner material 24 can have the exact same (or similar) shape as the gusset 18, but are slightly smaller in the lateral direction than the gusset 18, such that the layer of absorbent material 26 and the layer of liner material 24 can fit on the gusset 18 without hanging over the lateral edges 20 thereof.

As shown at 1008, the method includes attaching the left and right elastic bands 30, 130 along the respective left and right lateral edges of each of the layer of absorbent material 26 and the layer of liner material 24. This includes folding the left and right elastic bands 30, 130 around the respective left and right lateral edges of each of the layer of absorbent material 26 and the layer of liner material 24 and stitching the left and right elastic bands 30, 130 to the layer of absorbent material 26 and the layer of liner material 24 where the left and right elastic bands 30, 130 overlap the respective left and right lateral edges of each of the layer of absorbent material 26 and the layer of liner material 24. The layer of liner material 24 can also be bonded to the layer of absorbent material 26 (see adhesive tape 34, FIGS. 3-5) laterally inwardly of where the left and right elastic bands 30, 130 overlap and are stitched to the respective left and right lateral edges of each of the layer of absorbent material 26 and the layer of liner material 24. If this bonding is done before the left and right elastic bands 30, 130 are stitched to the layer of liner material 24 and the layer of absorbent material 26, it can help hold the layer of liner material 24 in place on the layer of absorbent material 26 while the two are stitched together along stitch lines 32. Such bonding with adhesive tape 34 also prevents excessive shifting of the layer of liner material 24 with respect to the layer of absorbent material 26 in the finished assembly. All of this is done before attaching the layer of waterproof material 28 to the left and right elastic bands 30, 130.

As shown at 1010, the method includes providing a layer of waterproof material 28 sized and shaped to fit on the gusset 18 and having left and right lateral edges configured to extend alongside the respective left and right lateral edges 20 of the gusset 18. Note that the layer of waterproof material 28 can have the exact same (or similar) shape as the gusset 18, but is slightly smaller in the lateral direction than the gusset 18 and larger in the lateral direction than the layer of absorbent material 26 and the layer of liner material 24. This way, the layer of waterproof material 28 can fit on the gusset 18 without hanging over the lateral edges 20 thereof, but can also extend over the stitch lines 32 connecting the elastic bands 30, 130 to the layer of absorbent material 26 and the layer of liner material 24. As shown at 1012, the method may include attaching the left and right lateral edges of the layer of waterproof material 28 to the respective left and right elastic bands 30, 130 adjacent the layer of absorbent material 26, such that the layer of absorbent material 26 is sandwiched between the layer of liner material 24 and the layer of waterproof material 28 (see FIGS. 3-5). While the attaching of the left and right elastic bands 30, 130 along the respective left and right lateral edges of each of the layer of absorbent material 26 and the layer of liner material 24 is done by stitching, the attaching of the left and right lateral edges of the layer of waterproof material 28 to the respective left and right elastic bands 30, 130 is done by bonding (see adhesive tape 36, FIGS. 3-5) so as to waterproof the stitch lines 32.

As shown at 1014, the method then includes placing the attached layer of liner material 24, layer of absorbent material 26, layer of waterproof material 28, and left and right elastic bands 30, 130 (together making up the absorbent assembly 11) on the gusset 18 on an inner face 13 of the main body 12 with the layer of waterproof material 28 adjacent the inner face 13 of the main body 12. The method includes subsequently attaching the left and right elastic bands 30, 130 to the respective left and right lateral edges 20 of the gusset 18 to couple the layer of liner material 24, the layer of absorbent material 26, and the layer of waterproof material 28 to the main body 12, as shown at 1016. Options for this step 1016 are discussed hereinabove with respect to step 912 of method 900.

Any of the above stitched connections could instead be made by bonding, and vice versa, although the present inventors have found that the connections specifically shown and described herein are suitable for strength and waterproofing purposes. For instance, the elastic bands 30, 130 are sewn to the fabric of the gusset 18 to provide a strong, washable connection that lasts longer than prior art bonded connections along the leg openings 22. The bonded connections between the elastic bands 30, 130 and the layer of waterproof material 28 ensure that liquid absorbed by the layer of absorbent material 26 does not leak out of the absorbent portion(s) of the garment 10, as might otherwise occur with a stitched connection between these pieces. The elastic bands 30, 130 can be treated with a water-repellant or waterproof finish that makes them resistant to water intrusion, thereby further ensuring that liquid stays inside the absorbent portion(s) of the garment 10. In one particular example, the elastic bands are SF7167/12/I/WP Y-folded elastic available from New Horizon Elastic Fabric Co., Ltd. of Dongguan, Guangdong Province, China. The thread used for stitching, especially at stitch lines 32, can also be treated with a water-repellant or waterproof finish.

The layer of liner material 24 can be any appropriate material that quickly absorbs liquid and pulls it away from the body. In one example, the layer of liner material 24 is a jersey knit material made of, for example, cotton or a cotton-synthetic blend. In one particular example, the layer of liner material 24 is a 91% cotton (40S), 9% elastane (40D) weft knit single jersey fabric. In another example, the layer of liner material 24 is a French terry knit. The layer of liner material 24 may be treated to provide special functionality, such as with a stain-release finish. In one example, the layer of liner material 24 is manufactured from polyester stain-release yarn, such as TOP CLEAN™ from Far Eastern New Century Corporation of Taiwan. For example, if the fabric is French terry knit, the terry side can be made of stain-release polyester yarn and the flat side can be made of regular polyester yarn. In another example, the layer of liner material 24 is treated on the non-skin side with a chemical that causes the fabric to pull liquid away from its skin-facing surface, and thereafter prevents the liquid from returning to the skin-facing side of the fabric. In still another example, a push-pull effect can be provided by yarn choice and fabric construction, such as if the skin-facing side of the layer of liner material 24 is constructed of yarn which is liquid-repellant, and the non-skin side is constructed of yarn that is liquid-absorbent. The liquid will be pushed by the liquid-repellant side to go through to the water-absorbent side, which simultaneously pulls the water away from the skin-facing, liquid-repellant side of the fabric. In still another example, the layer of liner material 24 is treated with an anti-microbial finish. In one particular example, the layer of liner material 24 can be treated with AGION™ AM Slurry available from Sciessent LLC of Wakefield, Mass. In another particular example, the layer of liner material 24 can be treated with Microban™ AEGIS™ AEM 5700, available from Microban International of Huntersville, N.C. Any of the above-noted functionalities and/or treatments of the layer of liner material 24 can be combined with one another.

The layer of absorbent material 26 can be any appropriate material that is capable of absorbing a volume of liquid up to, for example, 20-50 mL when provided in a size corresponding to a typical panty gusset. The layer of absorbent material 26 can be cotton, polyester, or blends thereof. Typically, the fabric will have a medium to heavy weight, ranging from 250 gsm-400 gsm. The layer of absorbent material 26 can be French terry fabric, with the non-flat side being maintained as longer loops of yarn or being shredded to create fleece. In one example, the layer of absorbent material 26 is a cotton/polyester French terry or fleece fabric with a water-absorbent finish, with the flat side facing the layer of liner material 24 and the non-flat (e.g., fleece) side facing the layer of waterproof material 28. In another example, the layer of absorbent material 26 is a two-layer bonded terry or fleece fabric, the flat side of which has a water-absorbent finish facing the layer of liner material 24 and the non-flat (e.g., fleece) side of which has a waterabsorbent finish facing the layer of waterproof material 28. In one particular example, the layer of absorbent material 26 is weft-knit French terry, the non-flat side of which has been shredded to form fleece, made of 84% cotton (30S), 16% polyester (10S) having a weight of 340 gsm, such as CO3F0024-BR01AV available from Far Eastern Polytex (VN) Ltd. of Binh Duong, Vietnam. In some examples, the layer of absorbent material 26 can be treated with a chemical, knit, and/or by way of yarn choice be constructed to provide a push-pull effect as was described herein above with respect to the layer of liner material 24. This may be particularly advantageous if no separate layer of liner material 24 is provided and the layer of absorbent material 26 directly touches the wearer's skin, as shown in FIG. 11. In one particular example, the dual-purpose liner/absorbent push-pull fabric is knit specifically to have a surface contact angle against the skin that tends to pull moisture away from the skin in the z-direction by capillary action. The side of the fabric that is configured to be located further from the skin may then spread the moisture throughout and along the far side of the fabric in the x- and y-directions, again by capillary action, such that the moisture is located on the far side of the fabric instead of the side that contacts the skin. In this regard, the dual-purpose liner/absorbent push-pull fabric as a whole is considered to absorb water by capillary action, even if it is knit from yarns of a hydrophobic polymer, such as, for example, polyester.

The layer of waterproof material 28 can be any suitable material that does not allow liquid to pass therethrough, or at least is resistant to liquid. In one example, the layer of waterproof material 28 comprises a fabric 28a bonded to a waterproof membrane 28b (see FIG. 3). The fabric 28a can be a sheer or semi-sheer fabric knitted from nylon, spandex, polyester, or blends thereof. The waterproof membrane 28b can be adhered, laminated, coated, or otherwise integrally formed on or bonded to the fabric 28a. The waterproof membrane 28b can be a polyurethane membrane or a thermoplastic polyurethane (TPU) membrane, which in one example comprises coffee oil to provide odor control. In one particular example, the layer of waterproof material 28 is weft-knit 100% polyester coated with a polyurethane membrane, and the membrane includes coffee oil. One such fabric is KB445S from Singtex Industrial Co., Ltd. of New Taipei City, Taiwan, which is 100% weft-knit polyester coated with a polyurethane membrane that comprises SCAFE™ Polyol. Alternatively, the layer of waterproof material 28 can be SCAFE™ AIRMEM™ from Singtex Industrial Co., Ltd. In another example, the layer of waterproof material 28 is a non-woven material coated with a waterproofing chemical.

The main body 12 fabric can be any fabric suitable for maintaining a close-to-body feel on the wearer's lower torso. For example, the main body 12 fabric can be a cotton-synthetic blend, a synthetic blend (of nylon, elastane, polyester, etc.), or any other known suitable fabric. In one particular example, the main body 12 fabric is a weft knit interlock nylon-elastane blend. In another particular example, the main body 12 fabric is a warp knit tricot nylon-elastane blend. The main body 12 fabric of the gusset 18 can be treated with or made from an odor-controlling material. For example, the fabric of the gusset 18 can be knitted partially or wholly with coffee-containing yarn, such as MYLITHE™ yarn from SCAFE™. Alternatively, the main body 12 fabric can be treated with an odor-controlling substance. Additionally or alternatively, the main body 12 fabric can be treated with a wicking finish that wicks moisture from the wearer's body to the outer face of the garment 10. Regardless of the fabric used for the gusset 18, any or all of the layers of material 24, 26, 28 can be treated with an antimicrobial finish as described herein above with respect to the layer of liner material 24 and/or the threads of the fabric can include an antimicrobial fiber, such as silver, to neutralize odors.

Referring back to FIG. 8, the front and back ends 25, 27 of the layer of liner material 24 (or the layer of absorbent material 26 if liner material is not provided) can be bonded to the fabric of the gusset 18 and/or front portion 14 or back portion 16 of the main body 12 by way of heat-activated adhesive finishing tape 50. Alternatively or additionally, the front and back ends 25, 27 of the layer of liner material 24 (or layer of absorbent material 26) can be sewn to the main body 12. The layer of waterproof material 28 can be bonded on its outer-facing side to the main body 12 at these locations as well. At these locations, the layer of waterproof material 28 can be bonded on its inner-facing side to the layer of absorbent material 26, which in turn can be bonded to the layer of liner material 24 (if present).

Any bonding noted hereinabove can be done by way of elastomeric heat-activated adhesive tape/film, such as that available from BEMIS™. Alternative methods of bonding include using spray adhesive, printed adhesive, mesh adhesive tape, ultrasonic bonding, and/or liquid glue.

The elastic bands 30, 130, 52 noted herein above can be braided, knitted, or woven elastic bands typically available for elasticizing the leg openings and/or waistband of garments.

In the above description, unless otherwise noted, "inner" refers to a face of a layer that faces the wearer when the garment is worn 10, while "outer" refers to a face of a layer that faces away from the wearer while the garment 10 is worn. The terms "left" and "right" and "front" and "back" are for reference purposes and are not limiting on the scope of the present disclosure or claims.

In the present description, certain terms have been used for brevity, clarity, and understanding. No unnecessary limitations are to be implied therefrom beyond the requirement of the prior art because such terms are used for descriptive purposes only and are intended to be broadly construed. The different assemblies described herein may be used alone or in combination with other systems. Various equivalents, alternatives, and modifications are possible within the scope of the appended claims. The methods herein are not limited to being performed in the order described, but could be performed in any logical order.

What is claimed is:

1. A garment comprising:
a main body including a front portion, a back portion, and a gusset connecting the front portion and the back portion, wherein the gusset has left and right lateral edges partially defining respective left and right leg openings of the garment;
a layer of absorbent material coupled to an inner face of the main body at least at the gusset;
a layer of waterproof material sandwiched between the main body and the layer of absorbent material;
a layer of liner material coupled to the layer of absorbent material such that the layer of absorbent material is sandwiched between the layer of liner material and the layer of waterproof material; and
left and right elastic bands coupling the layer of absorbent material and the layer of waterproof material to the main body along the respective left and right lateral edges of the gusset;
wherein the left and right elastic bands are folded around respective left and right lateral edges of each of the layer of liner material and the layer of absorbent material;
wherein the left and right elastic bands are stitched to the layer of liner material and the layer of absorbent material where the left and right elastic bands overlap the respective left and right lateral edges of each of the layer of liner material and the layer of absorbent material; and
wherein the layer of liner material is bonded to the layer of absorbent material laterally inwardly of where the left and right elastic bands overlap and are stitched to the respective left and right lateral edges of each of the layer of liner material and the layer of absorbent material.

2. The garment of claim 1, wherein the left and right elastic bands are stitched to the main body along the respective left and right lateral edges of the gusset laterally outwardly of where the left and right elastic bands overlap the respective left and right lateral edges of the layer of absorbent material.

3. The garment of claim 1, wherein the layer of waterproof material is bonded to each of the left and right elastic bands over stitches by which the left and right elastic bands are stitched to the respective left and right lateral edges of the layer of absorbent material.

4. The garment of claim 1, wherein each of the left and right elastic bands is stitched to itself laterally outwardly of and adjacent to where the left and right elastic bands overlap and are stitched to the respective left and right lateral edges of the layer of absorbent material.

5. The garment of claim 1, wherein the layer of waterproof material comprises a fabric bonded to a waterproof membrane, and the waterproof membrane comprises coffee oil.

6. The garment of claim 1, wherein the left and right elastic bands are stitched to the layer of absorbent material and bonded to the layer of waterproof material.

7. The garment of claim 1, wherein the main body is folded over the left and right elastic bands and attached to the left and right elastic bands at the respective left and right lateral edges of the gusset.

8. A method for manufacturing an absorbent garment, the method comprising:
providing a main body including a front portion, a back portion, and a gusset connecting the front portion and the back portion, wherein the gusset has left and right lateral edges configured to partially define respective left and right leg openings of the garment;
providing a layer of absorbent material sized and shaped to fit on the gusset and having left and right lateral edges configured to extend alongside the respective left and right lateral edges of the gusset;
folding left and right elastic bands around the respective left and right lateral edges of the layer of absorbent material;
attaching the left and right elastic bands along the respective left and right lateral edges of the layer of absorbent material by attaching the left and right elastic bands to the layer of absorbent material where the left and right elastic bands overlap the respective left and right lateral edges of the layer of absorbent material, wherein the attaching of the left and right elastic bands along the respective left and right lateral edges of the layer of absorbent material is done by stitching;
providing a layer of waterproof material sized and shaped to fit on the gusset and having left and right lateral edges configured to extend alongside the respective left and right lateral edges of the gusset;
attaching the left and right lateral edges of the layer of waterproof material to the respective left and right elastic bands by bonding the left and right lateral edges of the layer of waterproof material to the respective left and right elastic bands over stitches by which the left and right elastic bands are stitched to the respective left and right lateral edges of the layer of absorbent material; and
attaching the left and right elastic bands to the respective left and right lateral edges of the gusset to couple the layer of absorbent material and the layer of waterproof material to the main body.

9. The method of claim 8, further comprising attaching the left and right elastic bands to the main body along the respective left and right lateral edges of the gusset laterally outwardly of where the left and right elastic bands overlap the respective left and right lateral edges of the layer of absorbent material.

10. The method of claim 8, further comprising:
providing a layer of liner material sized and shaped to fit on the gusset and having left and right lateral edges configured to extend alongside the respective left and right lateral edges of the gusset;
attaching the left and right elastic bands along the respective left and right lateral edges of each of the layer of absorbent material and the layer of liner material before attaching the layer of waterproof material to the left and right elastic bands;
attaching the left and right lateral edges of the layer of waterproof material to the respective left and right elastic bands adjacent the layer of absorbent material, such that the layer of absorbent material is sandwiched between the layer of liner material and the layer of waterproof material;
placing the attached layer of liner material, layer of absorbent material, layer of waterproof material, and left and right elastic bands on the gusset on an inside face of the main body with the layer of waterproof material adjacent the inside face of the main body; and subsequently attaching the left and right elastic bands to the respective left and right lateral edges of the gusset.

11. The method of claim 10, further comprising:
folding the left and right elastic bands around the respective left and right lateral edges of each of the layer of absorbent material and the layer of liner material;
stitching the left and right elastic bands to the layer of absorbent material and the layer of liner material where the left and right elastic bands overlap the respective left and right lateral edges of each of the layer of absorbent material and the layer of liner material; and
bonding the layer of liner material to the layer of absorbent material laterally inwardly of where the left and right elastic bands overlap and are stitched to the respective left and right lateral edges of each of the layer of absorbent material and the layer of liner material.

12. The method of claim 8, further comprising folding the main body over the left and right elastic bands and attaching the main body to the left and right elastic bands at the respective left and right lateral edges of the gusset.

13. A method for manufacturing an absorbent garment, the method comprising:
providing a main body including a front portion, a back portion, and a gusset connecting the front portion and the back portion, wherein the gusset has left and right lateral edges configured to partially define respective left and right leg openings of the garment;
providing a layer of absorbent material sized and shaped to fit on the gusset and having left and right lateral edges configured to extend alongside the respective left and right lateral edges of the gusset;
providing a layer of liner material sized and shaped to fit on the gusset and having left and right lateral edges configured to extend alongside the respective left and right lateral edges of the gusset;
providing a layer of waterproof material sized and shaped to fit on the gusset and having left and right lateral edges configured to extend alongside the respective left and right lateral edges of the gusset;
attaching left and right elastic bands along the respective left and right lateral edges of each of the layer of absorbent material and the layer of liner material before attaching the layer of waterproof material to the left and right elastic bands;
attaching the left and right lateral edges of the layer of waterproof material to the respective left and right elastic bands adjacent the layer of absorbent material, such that the layer of absorbent material is sandwiched between the layer of liner material and the layer of waterproof material;
placing the attached layer of liner material, layer of absorbent material, layer of waterproof material, and left and right elastic bands on the gusset on an inside face of the main body with the layer of waterproof material adjacent the inside face of the main body; and
subsequently attaching the left and right elastic bands to the respective left and right lateral edges of the gusset to couple the layer of liner material, the layer of absorbent material, and the layer of waterproof material to the main body.

14. The method of claim 13, further comprising:
folding the left and right elastic bands around the respective left and right lateral edges of each of the layer of absorbent material and the layer of liner material;
stitching the left and right elastic bands to the layer of absorbent material and the layer of liner material where the left and right elastic bands overlap the respective left and right lateral edges of each of the layer of absorbent material and the layer of liner material; and
bonding the layer of liner material to the layer of absorbent material laterally inwardly of where the left and right elastic bands overlap and are stitched to the respective left and right lateral edges of each of the layer of absorbent material and the layer of liner material.

15. The method of claim 14, further comprising attaching the left and right elastic bands to the main body along the respective left and right lateral edges of the gusset laterally outwardly of where the left and right elastic bands overlap the respective left and right lateral edges of each of the layer of absorbent material and the layer of liner material.

16. The method of claim 13, wherein the attaching of the left and right elastic bands along the respective left and right lateral edges of each of the layer of absorbent material and the layer of liner material is done by stitching, and the attaching of the left and right lateral edges of the layer of waterproof material to the respective left and right elastic bands is done by bonding.

17. The method of claim 16, further comprising bonding the left and right lateral edges of the layer of waterproof material to the respective left and right elastic bands over stitches by which the left and right elastic bands are stitched to the respective left and right lateral edges of each of the layer of absorbent material and the layer of liner material.

* * * * *